(12) United States Patent
Schanze et al.

(10) Patent No.: US 9,005,540 B2
(45) Date of Patent: Apr. 14, 2015

(54) CONJUGATED POLYELECTROLYTE CAPSULES: LIGHT ACTIVATED ANTIMICROBIALS

(71) Applicants: University of Florida Research Foundation, Inc., Gainesville, FL (US); STC.UNM, Albuquerque, NM (US)

(72) Inventors: Kirk S. Schanze, Gainesville, FL (US); Motokatsu Ogawa, Sherman Oaks, CA (US); Jonathan Robert Sommer, Gainsville, FL (US); David G. Whitten, Albuquerque, NM (US); Thomas S. Corbitt, Albuquerque, NM (US)

(73) Assignees: University of Florida Research Foundation, Inc., Gainesville, FL (US); STC.UNM, Albuquerque, NM (US)

( * ) Notice: Subject to any disclaimer, the term of this patent is extended or adjusted under 35 U.S.C. 154(b) by 0 days.

(21) Appl. No.: 14/092,409

(22) Filed: Nov. 27, 2013

(65) Prior Publication Data
US 2014/0086795 A1 Mar. 27, 2014

Related U.S. Application Data

(62) Division of application No. 13/128,571, filed as application No. PCT/US2009/063715 on Nov. 9, 2009, now Pat. No. 8,618,009.

(60) Provisional application No. 61/112,867, filed on Nov. 10, 2008.

(51) Int. Cl.
*A61L 2/00* (2006.01)
*H01B 1/04* (2006.01)
(Continued)

(52) U.S. Cl.
CPC ............... *A01N 25/28* (2013.01); *A01N 25/00*
(Continued)

(58) Field of Classification Search
CPC ........... A61L 9/012; A61L 9/20; A61L 9/205; B01J 13/00; B08B 7/0035; C02F 1/288; C02F 1/32

USPC .............. 422/1, 22, 28, 123, 186, 186.3, 261; 252/503, 508, 316, 62.2; 977/172, 903; 502/8; 510/349; 426/89; 424/490, 408; 428/402, 402.21, 402.24
See application file for complete search history.

(56) References Cited

U.S. PATENT DOCUMENTS 4,251,386 A * 2/1981 Saeki et al. .................... 264/4.7
(Continued)

FOREIGN PATENT DOCUMENTS

WO WO-2010/054304 A2 5/2010

OTHER PUBLICATIONS

"U.S. Appl. No. 13/128,571, Response filed May 13, 2013 to Non Final Office Action mailed Feb. 13, 2013", 12 pgs.
(Continued)

*Primary Examiner* — Monzer R Chorbaji
(74) *Attorney, Agent, or Firm* — Schwegman Lundberg & Woessner, P.A.

(57) ABSTRACT

Hollow conjugated polyelectrolyte (HCPE) microcapsules contain at least one conjugated polyelectrolyte and at least one other polyelectrolyte of complementary charge and the microcapsule has a hollow core. The conjugated polyelectrolyte is a polymer with a multiplicity of charged repeating units where a portion of the charged repeating units form a pi-conjugated sequence. The complementary polyelectrolyte is a polymer with a complementary charged repeating unit to the charged repeating units of the conjugated polyelectrolyte. The HCPE microcapsules can be formed by successively coating a sacrificial core with alternating layers of complementary polyelectrolytes, at least one of which is a conjugated polyelectrolyte. The sacrificial core can be removed to form the hollow center of a HCPE microcapsule. The HCPE microcapsules can be contacted with a medium containing microbes where the HCPE microcapsules associate with the microbes and efficiently kill the microbes when irradiated with light or other electromagnetic radiation.

9 Claims, 5 Drawing Sheets

(51) Int. Cl.
- *A01N 25/28* (2006.01)
- *A01N 25/00* (2006.01)
- *A01N 25/10* (2006.01)
- *A01N 25/34* (2006.01)
- *A01N 43/90* (2006.01)
- *A61L 2/23* (2006.01)

(52) U.S. Cl.
CPC ........ (2013.01); *A01N 25/10* (2013.01); *A01N 25/34* (2013.01); *A01N 43/90* (2013.01); *A61L 2/23* (2013.01); *Y10S 977/712* (2013.01); *Y10S 977/903* (2013.01)

(56) References Cited

U.S. PATENT DOCUMENTS

| | | | |
|---|---|---|---|
| 8,618,009 | B2 | 12/2013 | Schanze et al. |
| 2005/0148254 | A1* | 7/2005 | Lu et al. ............ 442/123 |
| 2007/0215841 | A1* | 9/2007 | Ford et al. ............ 252/503 |
| 2011/0293470 | A1 | 12/2011 | Schanze et al. |

OTHER PUBLICATIONS

"U.S. Appl. No. 13/128,571, Response filed Nov. 19, 2012 to Restriction Requirement mailed Oct. 17, 2012", 6 pgs.
"U.S. Appl. No. 13/128,571, Non Final Office Action mailed Feb. 13, 2013", 10 pgs.
"U.S. Appl. No. 13/128,571, Notice of Allowance mailed Aug. 28, 2013", 9 pgs.
"U.S. Appl. No. 13/128,571, Preliminary Amendment filed May 10, 2011", 5 pgs.
"U.S. Appl. No. 13/128,571, Restriction Requirement mailed Oct. 17, 2012", 6 pgs.
"International Application Serial No. PCT/US2009/063715, International Preliminary Report on Patentability mailed May 10, 2011", 6 pgs.
"International Application Serial No. PCT/US2009/063715, International Search Report mailed May 27, 2010", 4 pgs.
"International Application Serial No. PCT/US2009/063715, Written Opinion mailed May 27, 2010", 5 pgs.
Chemburu, S., et al., "Light-Induced Biocidal Action of Conjugated Polyelectrolytes Supported on Colloids", *Langmuir*, 24, (2008), 11053-11-62.
Choi, W. S., et al., "Synthesis of Two Types of Nanoparticles in Polyelectrolyte Capsule Nanoreactors and Their Dual Functionality", *J. Am. Chem. Soc.*, 127, (2005), 16136-16142.
De Geest, B. G., et al., "Release mechanisms for polyelectrolyte capsules", *Chem. Soc. Rev.*, 36, (2007), 636-649.
Lee, H., et al., "Shell Cross-Linked Hyaluronic Acid/Polylysine Layer-by-Layer Polyelectrolyte Microcapsules Prepared by Removal of Reducible Hyaluronic Acid Microgel Cores", *Biomacromolecules*, 8, (2007), 3705-3711.
Lu, L., et al., "Biocidal Activity of a Light-Absorbing Fluorescent Conjugated Polyelectrolyte", *Langmuir*, 21, (2005), 10154-10159.
Tiller, J. C., et al., "Designing surfaces that kill bacteria on contact", *Proc. Natl. Acad. Sci. USA*, 98(11), (May 22, 2001), 5981-5985.
Tong, W., et al., "Single Polyelectrolyte Microcapsules Fabricated By Glutaraldehyde-Mediated Covalent Layer-By-Layer Assembly", *Macromol. Rapid Commun.*, 27, (2006), 2078-2083.
Wang, Z., et al., "Preparation and application of single polyelectrolyte microcapsules possessing tunable autofluorescent properties.", *Colloids and Surfaces A: Physiochemical and Engineering Aspects*, 329, (2008), 58-66.
Zhu, H., et al., "Synthesis of Size-Controlled Monodisperse Manganese Carbonate Microparticles as Templates for Uniform Polyelectrolyte Microcapsule Formation", *Chem. Mater.*, 17, (2005), 2323-2328.

* cited by examiner

CONJUGATED POLYELECTROLYTE CAPSULES: LIGHT ACTIVATED ANTIMICROBIALS

CROSS-REFERENCE TO A RELATED APPLICATION(S)

The present application is a divisional of U.S. patent application Ser. No. 13/128,571, filed Aug. 8, 2011, which is a U.S. National Stage application under 35 U.S.C. §371 of International Patent Application No. PCT/US2009/063715, filed Nov. 9, 2009, which claims the benefit of priority to U.S. Provisional Patent Application No. 61/112,867, filed Nov. 10, 2008, all of which are incorporated herein by reference in their entirety.

BACKGROUND OF THE INVENTION

Surfaces with antimicrobial properties are of interest for medical facilities, medical devices, and even homes and household items to reduce the transmission of diseases and other malaise from one organism to another organism through common contact with the surface. Microbes generally have a limited lifetime on a surface; however that lifetime is generally for at least a few hours and is often in the order of days. Even when the microbes survive for hours significant contact can occur over that period. The most prevalent technologies used for antimicrobial surfaces include: silver ion technology; organic biocides in coatings or incorporated into objects; and cationic biocides covalently bonded to a reactive silicone compounds.

Silver ion technology in its simplest form is a coating system formed by binding silver ions to a fine ceramic powder, dispersed in a carrier. The silver ions, which can interrupt critical functions of microorganisms, are then exchanged with other ions when the surface comes into contact with aqueous fluids. This technology has been used to treat steel ducting and components in HVAC systems, building materials, laminates, floors, walls, paints, carpets, cubicle curtains, lockers, safety cabinets, bedpans, sack holders, soap dispensers, keypads, medical devices, wound dressings and implants.

Organic biocides have been incorporated into plastic and fabrics during manufacture. The concentration of biocide is optimized to provide adequate protection. Many different organic biocides are now in use, some specially selected for specific applications. Some of the earliest applications involved combating the growth of odor causing bacteria on medical devices. Applications for the building industry include wall laminates, for hospital environments include bedding, bed frames, carts for transport of medication, linens, hand rails, pulls, trims, door handles, slings, hoists, window blinds, dental trays, incise drapes, wound dressings, keyboards and other equipment.

Biocides covalently bonded to a reactive silicone compound are fixed onto a surface as an extremely thin film with little effect to the physical properties of the surface. Fixation of the biocide is important where toxicity, taint and other organoleptic aspects are of concern. This method is a bacteriostatic surface treatment that allows and requires normal cleaning procedures to maintain the biocidal activity of the surface. The technology has been used for treatment of bedsheets, hospital garments, curtains, floor and wall materials, air filtration systems, medical devices, bandages, surgical instruments and implants. The technique has been used to prevent biofilm growth on catheters, stents, contact lenses and endotracheal tubes.

These technologies can suffer from toxicity to organisms other than the microbes or promote formation of resistant strains of the microbes. Recently, light activated antimicrobial agents such as the dye indocyanine green have been found to be highly potent only when light activated, harmless to the organism and not believed to promote resistance due to the light only toxicity to the microbes. Polymeric materials generally display low toxicity to organisms and can be readily fixed to surfaces. Light activated antimicrobial polymeric materials have been reported, generally consisting of small molecule antimicrobials included in a polymeric carrier, but are not covalently bonded to the polymer. Antimicrobial polymers have the potential to exist in many different structural forms where enhancements, such as the surface area to volume, can significantly increase their activity toward microbes relative to surface fixed antimicrobial agent. Hence, a polymer that is a high molecular weight light activated antimicrobial agent is an attractive solution to many limitations of present antimicrobial system.

BRIEF SUMMARY OF THE INVENTION

An embodiment of the invention is a hollow conjugated polyelectrolyte (HOPE) microcapsule where at least one conjugated polyelectrolyte is in association with at least one complementary polyelectrolyte in the shape of a microcapsule with a hollow core. The conjugated polyelectrolyte is a polymer with a multiplicity of charged repeating units with at least a portion of the charged repeating units forming a pi-conjugated sequence. The complementary polyelectrolyte is one where a plurality of repeating units has a charge that is opposite the charge on the repeating units of the conjugated polyelectrolyte, such that charges on the polyelectrolytes associate through ion-pairing of some of the repeating units of the two polyelectrolytes. The complementary polyelectrolytes can also be a conjugated polyelectrolyte. The HCPE microcapsules can be 0.5 to 100 μm in cross-section, for example about 4 to about 6.mu·m in cross-section, and can be monodispersed in size distribution. In one embodiment of the invention, the HCPE microcapsule can be formed from the complementary conjugated polyelectrolytes PPE-$SO_3^-$ and PPE-$4^+$ A plurality of polyelectrolytes can exist as a plurality of layers where adjacent layers have complementary charges on the polymer.

Another embodiment of the invention is a method of preparing (HCPE) microcapsules where a sacrificial core is coated with a polyelectrolyte layer and additionally coated on the exterior polyelectrolyte layer with an additional polyelectrolyte layer. The additional polyelectrolyte has repeating units of a complementary charge to the polyelectrolyte upon which it is deposited. Optionally, successive additional coatings of additional complementary polyelectrolytes can be deposited where the deposited polyelectrolyte has repeating units of a complementary charge to the polyelectrolyte upon which it is deposited. At least one of the polyelectrolytes used to form the HCPE microcapsule is a conjugated polyelectrolyte. After deposition of the layers, the sacrificial cores can be removed to leave the (HCPE) microcapsules.

In one embodiment of the invention, the sacrificial core is a salt particle with low water solubility. After formation of the conjugated polyelectrolyte (CPE) microcapsule, the core can be removed by dissolving a species formed from the salt particle by contacting the salt particle with an acid, base, metal complexing agent or any combination thereof to form the HCPE microparticle. For example, a monodispersed $MnCO_3$ particle can be prepared and a PPE-$SO_3^-$ conjugated polyelectrolyte can be coated from aqueous solution on the $MnCO_3$ core, a complementary PPE-4$^+$ conjugated polyelectrolyte can be coated from aqueous solution on the PPE-$SO_3^-$ conjugated polyelectrolyte and EDTA can be added to decompose the $MnCO_3$ sacrificial core and dissolve the resulting complexed MnEDTA salt.

In another embodiment of the invention, (HCPE) microcapsules can be used in a method for killing microbes where a plurality of hollow conjugated polyelectrolyte (HCPE) microcapsules is contacted with a medium suspected of containing microbes and irradiating the (HCPE) microcapsules with visible light, ultraviolet light or other electromagnetic radiation to kill the microbes contacted by one or more of the polyelectrolyte (HCPE) microcapsules. The medium can be an aqueous medium.

DETAILED DESCRIPTION OF THE INVENTION

Embodiments of the invention are directed to hollow conjugated polyelectrolyte (HCPE) microcapsules that have antimicrobial properties when irradiated with electromagnetic radiation. In an embodiment of the invention, the HCPE microcapsules display effective antimicrobial action against bacteria, viruses, fungi or other microbes that associate with the HCPE microcapsules, which acts as an efficient trap where the trapped microbes are efficiently killed upon irradiation. The microbes can be entrapped within or attached to the external surface of the HCPE microcapsules. Not to be bound by a theoretical mechanism, the light-activated antimicrobial activity is consistent with the generation of singlet oxygen and possibly successor reactive oxygen intermediates at the photoexcited HCPE microcapsule upon irradiation.

In one embodiment of the invention, the HCPE microcapsules comprise a plurality of layers of polyelectrolytes of complementary charge where at least one polyelectrolyte is a conjugated polyelectrolyte. The layers are formed about a sacrificial core. In one embodiment of the invention the sacrificial cores are monodispersed in size to allow the formation of monodispersed HCPE microcapsules upon removal of the sacrificial cores.

The conjugated polyelectrolytes can be adsorbed on the sacrificial cores in a layer-by-layer fashion were the first layer can be either a cationic polyelectrolyte or an anionic polyelectrolyte. Although, two layers are sufficient to form the HCPE microcapsules, in other embodiments of the invention additional layers can be formed to yield multilayer HCPE microcapsules. In other embodiments of the invention, one or more conjugated polyelectrolytes can be bound to a non-conjugated polyelectrolyte, where the conjugated polyelectrolyte is capable of contacting an external bacteria or other microbial agent.

The sacrificial cores can be of any material that effectively associates with a polyelectrolyte and can be removed after construction to form the HCPE microcapsules. The core can be any particulate material or suspended liquid droplet that can promote the formation of a layer of an anionic or cationic polyelectrolyte on its surface, yet can be removed after formation of the desired number of polyelectrolyte layers on the surface. The core can be removed in any fashion that does not damage the HCPE microcapsules, for example the removal can be any method of dissolving, vaporizing, and/or degradation of the sacrificial core. In one embodiment of the invention the sacrificial core is relatively monodispersed in size. The monodispersed cores have non aggregated cores that have a standard deviation in size that is less than about 25% of the mean size, for example, less than 10% of the mean size.

In one embodiment of the invention, the sacrificial core is a salt particle that is of low solubility in water. Salts that can be used as the sacrificial cores include, but are not restricted to, carbonates, oxides, chalcogenides, and other salts. Useful salts include those that can be decomposed using an acid or base, or dissolved using a metal complexing agent, such as ethylenediaminetetraacetic acid (EDTA). The salt particle can be prepared by any method where the size can be restricted to a particular desired size range, for example less than 100 µm, for example 50, 45, 40, 35, 30, 25, 20, 15, 10, 9, 8, 7, 6, 5, 4, 3, 2, 1, 0.5 or 0.1 µm. Where, in the lower limits, what is referred to as a microcapsule for purposes of the invention can be a nanocapsule where the size is less than 1 µm. The particles can be selected by size using sieves for isolation of a particular size distribution out of a source that is polydispersed in size or particles of a selected size and/or distribution can be achieved by direct formation of particles by any method where nucleation and propagation of particle formation can be controlled. For example, monodispersed metal carbonate particles, for example $MnCO_3$ particles, can be formed as taught in Zhu et al., Chem. Mater. 2005, 17, (9), 2323-8, and is incorporated herein by reference. For example, the standard deviation in size can be less than 10% of a mean size that can be, for example, less than 10 µm in size. To remove $MnCO_3$ particles and leave HCPE microcapsules, decomposition and dissolution of the $MnCO_3$ with an EDTA solution results in the loss of $CO_2$ with the liberation of MnEDTA to the aqueous solution.

According to embodiments of the invention, the conjugated polyelectrolytes can be poly(phenylene ethynylene), poly(phenylene vinylene), poly(acetylene), poly(phenylene), poly(pyrrole), poly(furan), poly(thiophene) or any other conjugated polymer or copolymer where a sufficient number of side groups include non-hydrolyzable ionic side groups where each ionic side group can contain one or more atoms having a unit charge centered. The side groups can contain anionic groups, such as sulfonate, phosphonate, carboxylate, oxide, sulfide, sulfinate, phosphonate, thiosulfate, or any other anionic group that can be attached via a substituted or unsubstituted linking group, such as an alkylene, phenylene, or alkylene or phenylene group including one or more heteroatoms that links the ionic group to the polymer backbone in a regular or random manner. The side groups can contain cationic groups, such as ammonium, pyridinium, phosphonium, or metal ions captured by a crown ether, cryptand, or carcerand units or any other cationic group that can be attached via a substituted or unsubstituted linking group, such as an alkylene, phenylene, or an alkylene or phenylene group including one or more heteroatoms that links the ionic group to the polymer backbone in a regular or random manner.

In embodiments of the invention an anionic conjugated polyelectrolyte can be deposited as a layer on the sacrificial core, followed by deposition of a complementary cationic conjugated polyelectrolyte. The repeating units of the two complementary conjugated polyelectrolyte can be identical except for the ionic side group, for example with the same conjugated repeating unit structure, the position of the ionic side groups can be equally spaced along the conjugated backbone with an equivalent charge on every side group. In other embodiments of the invention, the side groups can have unequal charge, for example a cationic side group can have a charge of +2 and the paired anionic side group of the complementary conjugated polyelectrolyte can have a charge of −1. The sacrificial core can stabilize the microcapsule shape such that the HCPE microcapsule upon removal of the core can slowly undergo a metamorphosis in shape or the HCPE microcapsule can retain the shape resulting after deposition of the polyelectrolytes on the core.

In some embodiments of the invention, one of the complementary polyelectrolytes need not be conjugated. For example, a non-conjugated anionic polyelectrolyte, such as polystyrene sulfonate, can be paired with a cationic conjugated polyelectrolyte, or a non-conjugated cationic polyelectrolyte, such as poly(N-alkyl-4-vinylpyridinium halide), can be paired with an anionic conjugated polyelectrolyte.

In embodiments of the invention, contact is made between suspensions of the HCPE microcapsules with microbes that result in an association. The HCPE microcapsules can be isolated, or aggregated into clusters in these contacted suspensions. For example, a typical mixture can display dimeric and other larger clusters of HCPE microcapsules. For example clusters of 2, 4 and up to 12 HCPE microcapsules can form. Clustered HCPE microcapsules can form stronger associations with the microbes. The HCPE microcapsules can form features that increase the surface area of the paired conjugated polymers. For example, a HCPE microcapsule can radiate fibrils in the presence of microbes to increase the surface area of the HCPE microcapsule. Trapping of microbes can be enhanced by the formation of fibrils or sheet-like structures.

Association of the microbes with the HCPE microcapsules does not result in high killing of the microbes in the dark. However, upon irradiation with light, the microbes are very effectively killed, where the strength of the association and the rate and extent of killing is enhanced by clustering of the HCPE microcapsules and microbes. Irradiation can be for short periods of time to extended periods of time. For example, the irradiation can be for less than 1 minute to more than 4 hours. Irradiation can be carried out concurrently or subsequently to the mixing of the HCPE microcapsules and the microbes. Irradiation can be carried out with a broad spectrum of light or with a portion of the spectrum which promotes the killing. Light in the visible or ultraviolet range of the spectrum may be employed. As different HCPE microcapsules can be generated from various CPEs the necessary range must be established for a specific HCPE microcapsule, which can be readily determined by normal experimentation by one skilled in the art.

Materials and Methods
Preparation of MnCO₃ Microparticles

Figure 1:
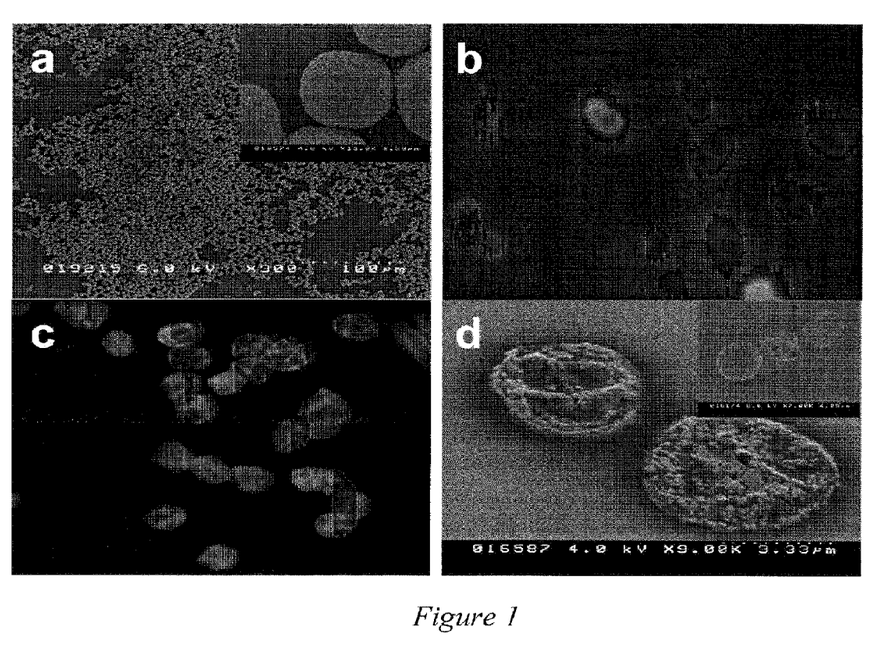
FIG. 1 shows scanning electron and fluorescence microscope images at different stages of preparation of HCPE microcapsules where: (a) shows a SEM image of a $MnCO_3$ core before coating; (b) shows a fluorescence microscope image of CPE microparticles before removal of the sacrificial cores; and (c) shows a fluorescence microscope image of a flattened HCPE microcapsule with a creased surface; (d) shows a SEM image of a flattened HCPE microcapsule with a creased surface.

Monodispersed $MnCO_3$ microparticles were prepared where nanoparticles from dilutes salt solutions of $MnSO_4$ and $NH_4HCO_3$ were used as "nanoseeds" to initiate crystal growth without significant nucleation during the crystal growth process such that relatively monodispersed $MnCO_3$ microparticles were formed. The nanoseeds were suspended in a $MnSO_4$ solution which was vigorously mixed with a $NH_4HCO_3$ solution to give either smooth cubical $MnCO_3$ particles or spherical particles depending upon the rate of mixing using a stirrer. The $MnCO_3$ microparticles were 4 to 6 μm in cross section. Typical mean particle size was 4.5 to 5.0 .mu·m with a standard deviation of 0.3 to 0.5 μm, as indicated by scanning electron microscopy (SEM) and dynamic light scattering (DLS) analysis. Spherical shaped particles can be seen in the SEM image shown in FIG. 1(a) where the particles display a rough surface with an aggregation of small rectangular crystals forming the spherical particles. DLS data show monodispersed particles in the 4 to 6 .mu·m range where 92 to 98% of the particles are isolated particles and 2 to 8% of the particles forming aggregates in the 8 to 12 μm range. An exemplary DLS trace shows a mean particle size of 4.568 μm with a standard deviation of 0.387 μm representing 98% of the sample with 2% aggregate.

Absorption of CPEs on MnCO₃ Microparticles

Figure 2:
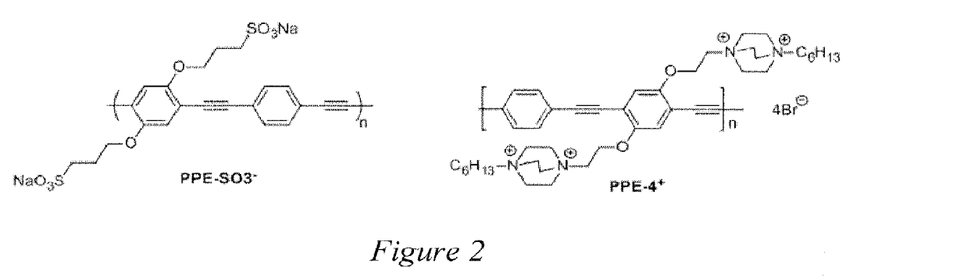
FIG. 2 shows the chemical structure of an anionic conjugated polyelectrolyte (PPE-$SO_3^-$) according to an embodiment of the invention and a cationic conjugated polyelectrolyte (PPE-4$^+$) according to an embodiment of the invention.

CPEs were formed by a Layer-by-Layer deposition technique. Suspensions of $MnCO_3$ particles in 0.5 M NaCl were prepared with vigorous stirring and sonication of the suspensions. A CPE, PPE-$SO_3^-$, shown in FIG. 2, was introduced from solution to the suspension and the suspension stirred for 15 minutes. After centrifugation and washing of the particles, with 0.2 M NaCl the particles were resuspended in 0.5 M NaCl followed by addition of the complementary CPE, PPE-$4^+$, shown in FIG. 2, solution to the suspension to form a second CPE layer. The formation of 4 bilayers on the particles was followed by fluorescence and confocal microscopy analysis. Fluorescence microscopy showed emissive CPE layers and uniformly coated microparticles, as can be seen in FIG. 1(b). Confocal microscopy images revealed, in addition to the fluorescent characteristics of the particles, uncoated $MnCO_3$ surfaces refracted light form particles.

HCPE Formation

Coated particles were treated with a 0.2 M EDTA solution in 1.5 to 3 mL centrifuge vials. The formation of bubbles occurred upon introduction of the EDTA solution. The particles were flushed with solution using a pipette and centrifuged after 30 minutes and treated a second time with 0.2 M EDTA. Upon complete removal of the $MnCO_3$, HCPE capsules were isolated by three cycles of washing with purified water and centrifugation. Analysis of the HCPE microcapsules by fluorescence microscopy with a $100_X$ oil immersion objective resulted in images where small creased features appeared on the HCPE walls, as shown in FIG. 1(c). The HCPE microcapsules assumed a flattened appearance, as shown in FIG. 1(d). The HCPE microcapsules retained the cross section of 4-6 μm.

Preparation of Bacteria and Association with HCPE Microparticles

Figure 3:
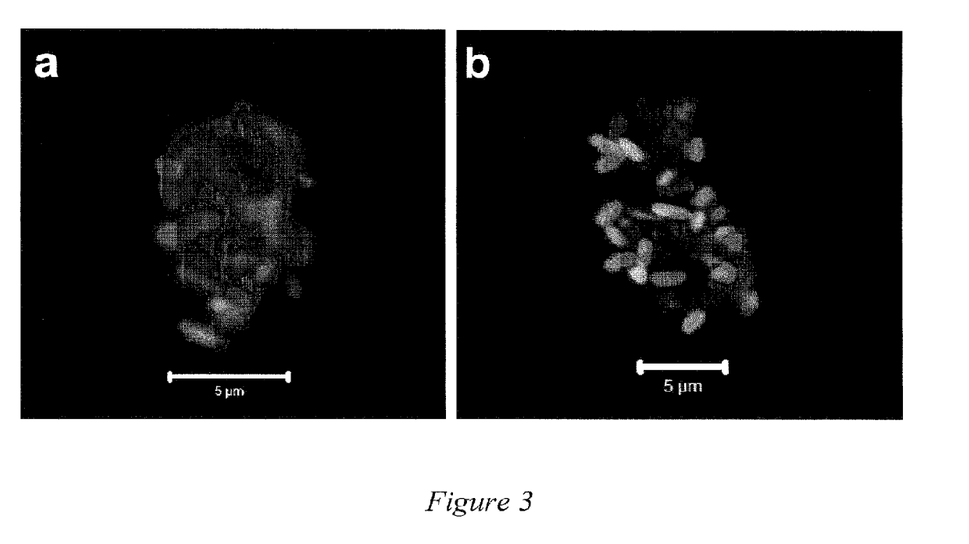
FIG. 3 shows confocal microscope images of HCPE microcapsules with (a) live trapped bacteria before irradiation and (b) dead trapped bacteria after 15 minutes of irradiation.

*Pseudomonas aeruginosa* and *Cobetia marina* were raised in a chemostat as described in Chemburu et al., *Langmuir* 2008, 24, (19), 11053-62. Confocal fluorescence microscopy was used to monitor the association of the bacteria with the HCPE microparticles. Bacterial viability was determined by staining with a 1:1 mixture of SYTO 60 and SYTOX green stains from Molecular Probes. The DNA stains produced red (~650 nm) and green (~530 nm) emissions for live and dead bacteria respectively. The mixing of a suspension of *Pseudomonas aeruginosa* with a suspension of HCPE microcapsules results in the effective capture of the bacteria. FIG. 3(a) shows that bacteria associate on the surface and within the interior of the HCPE microcapsules. A ratio of more than 7 to 1 was observed for live to dead bacteria associated with the HCPE microcapsules.

Light Induced Anti-Microbial Action

Figure 4:
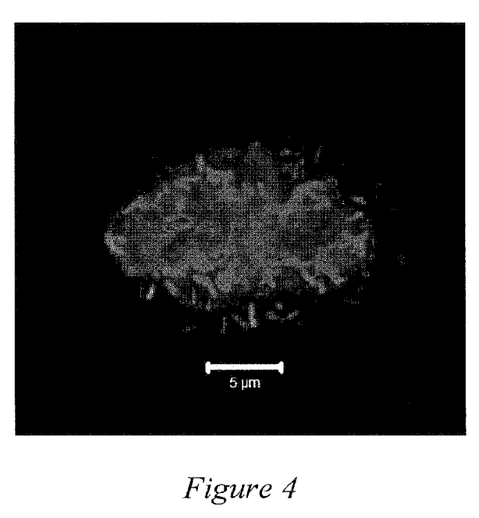
FIG. 4 shows a central slice of large clusters with entrapped dead bacteria after 1 hour exposure to white light.

Irradiation of the HCPE microcapsules associated with the bacteria resulted in rapid killing of the bacteria. FIG. 3(b) shows a fused pair of HCPE microcapsules associated with *Pseudomonas aeruginosa* that have been irradiated with visible light. The green fluorescence indicated that most of the bacteria are dead. When *Pseudomonas aeruginosa* is associated with paired HCPE microcapsules visible light irradiation results in the rapid killing of most bacteria. When HCPE microcapsules are agglomerated into larger clusters the killing efficiency of the HCPE microcapsules is enhanced. FIG. 4 shows large clusters of 4 to 12 HCPE microcapsules, particularly abundant are clusters of 4 HCPE microcapsules in a tetrahedral orientation to each other. The killing of all *Pseudomonas aeruginosa* is apparent in FIG. 3. In all cases oxygen was present. Otherwise equivalent filled CPE microcapsules show inferior killing of microbes upon irradiation.

Structural Evolution of HCPE Microcapsules with Bacteria

Figure 5:
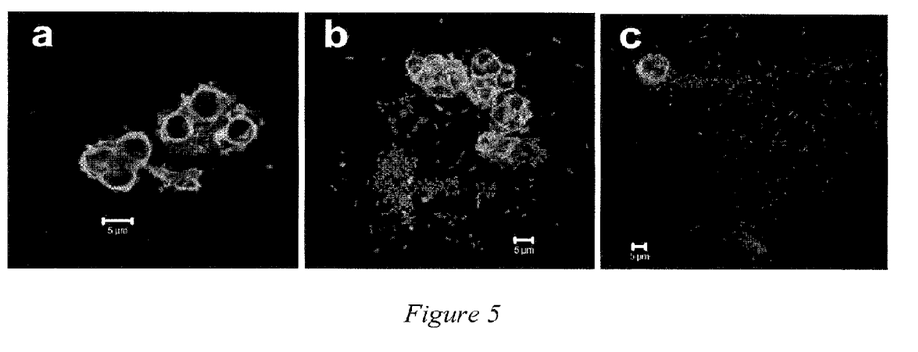
FIG. 5 shows HCPE microcapsules with entrapped bacteria where the microcapsules display (a) fibrillar structures, filaments, and (b) and (c) sheet-like structures.

Over a period of several hours the HCPE microcapsules undergo a structural evolution that promotes strong association with bacteria. FIG. 5 illustrates that with time fibrillar structures extend from the microcapsules, as clearly shown in FIG. 5(a). These fibrillar structures, and sheet-like structures of FIG. 5(b)-(c), are highly effective at capturing bacteria. These structures appear to have a hydrogel consistency.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A hollow conjugated polyelectrolyte microcapsule comprising:
    at least one conjugated polyelectrolyte comprising a multiplicity of charged repeating units wherein the repeating units are of a first electrical charge type, and at least a portion of said charged repeating units are pi-conjugated; and
    at least one complementary polyelectrolyte comprising a plurality of charged repeating units having complementary charge to said first electrical charge type of wherein the said conjugated polyelectrolyte and said complementary polyelectrolyte associate as a microcapsule with a hollow core within said microcapsule, wherein said at least one conjugated polyelectrolyte and said at least one complementary polyelectrolyte each comprise one or more layers and wherein said microcapsule comprises a plurality of layers, and wherein each said layer comprising said complementary electrolyte comprises a counter ion of opposite charge to a counter ion of each said layer comprising said conjugated polyelectrolyte.

2. The hollow conjugated polyelectrolyte microcapsule of claim 1, wherein said microcapsule is 0.5 to 100 μm in cross-section diameter.

3. The hollow conjugated polyelectrolyte microcapsule of claim 2, wherein said microcapsule is about 4 to about 6 μm in cross-section diameter.

4. The hollow conjugated polyelectrolyte microcapsule of claim 1, wherein said conjugated polyelectrolyte comprises $PPE\text{-}SO_3^{31}$ or $PPE\text{-}4_+$.

5. The hollow conjugated polyelectrolyte microcapsule of claim 4, wherein said complementary polyelectrolyte respectively comprises $PPE\text{-}4^+$ or $PPE\text{-}SO_3^-$.

6. The hollow conjugated polyelectrolyte microcapsule of claim 1, wherein said microcapsule is monodispersed in size.

7. A method for killing microbes comprising the steps of:
    providing a plurality of hollow conjugated polyelectrolyte microcapsules of claim 1;
    contacting said hollow conjugated polyelectrolyte microcapsules with a medium potentially containing microbes; and
    irradiating said hollow conjugated polyelectrolyte microcapsules with electromagnetic radiation, wherein the microbes are killed.

8. The method of claim 7, wherein said medium comprises an aqueous medium.

9. The method of claim 7, wherein said electromagnetic radiation comprises visible or ultraviolet radiation.

* * * * *

UNITED STATES PATENT AND TRADEMARK OFFICE
CERTIFICATE OF CORRECTION

PATENT NO. : 9,005,540 B2
APPLICATION NO. : 14/092409
DATED : April 14, 2015
INVENTOR(S) : Schanze et al.

It is certified that error appears in the above-identified patent and that said Letters Patent is hereby corrected as shown below:

In the Claims

In column 8, line 20, in Claim 3, delete "polyelectrolytemicrocapsule" and insert --polyelectrolyte microcapsule--, therefor In column 8, line 25, in Claim 4, delete "PPE-SO$_3^{31}$ or PPE-4$_+$." and insert --PPE-SO$_3^-$ or PPE-4$^+$.--, therefor Signed and Sealed this
Third Day of November, 2015

Michelle K. Lee
*Director of the United States Patent and Trademark Office*